United States Patent [19]

Karrer

[11] Patent Number: 5,141,956
[45] Date of Patent: Aug. 25, 1992

[54] PESTICIDAL COMPOSITION

[75] Inventor: Friedrich Karrer, Zofingen, Switzerland

[73] Assignee: Ciba-Geigy Corporation, Ardsley, N.Y.

[21] Appl. No.: 540,045

[22] Filed: Jun. 19, 1990

[30] Foreign Application Priority Data

Jun. 21, 1989 [CH] Switzerland ............... 2311/89

[51] Int. Cl.$^5$ .................. A01N 25/32; C07C 271/00
[52] U.S. Cl. ........................ 514/486; 560/12; 560/27; 560/30; 424/406; 514/476; 514/478; 514/487
[58] Field of Search ............. 560/12, 27, 30; 424/406; 514/476, 478, 486, 487

[56] References Cited

U.S. PATENT DOCUMENTS

| 4,215,139 | 7/1980 | Fischer et al. | 424/300 |
| 4,413,010 | 11/1983 | Zurflüsh | 424/300 |

FOREIGN PATENT DOCUMENTS

| 0004334 | 3/1979 | European Pat. Off. |
| 38322656 | 4/1989 | Fed. Rep. of Germany |
| 2609713 | 7/1988 | France |
| 2084574 | 9/1981 | United Kingdom |

OTHER PUBLICATIONS

Abstracts, The Sixth Internatonal Congress of Pesticide Chemistry, 1UPAC, Aug. 10-15, 1986, Ottawa, Canada.
J. Econ. Entomol. 80:126-130 (1987), C. H. Schaefer et al (1987).

Primary Examiner—Jose G. Dees
Assistant Examiner—Porfirio Nazario
Attorney, Agent, or Firm—Kevin T. Mansfield; Edward McC. Roberts

[57] ABSTRACT

Ethyl 2-[4-(3-chlorophenoxy)phenoxy]ethylcarbamate is suitable controlling phytophagous cicadas in rice crops and fruit pests such as leaf rollers, citrus fruit pests such as scale insects, and vegetable and cotton pests such as white flies and noctuids.

14 Claims, No Drawings

PESTICIDAL COMPOSITION

The present invention relates to ethyl 2-[4-(3-chlorophenoxy)phenoxy]ethylcarbamate, to its preparation, to compositions which contain this compound and to the use thereof for controlling phytophagous cicadas in rice crops and fruit pests. The carbamate used in the practice of this invention is especially suitable for controlling rice cicadas of the family of the Delphacidae with the genus Nilaparvata and the of the family of the Cidadellidae with the genus Nephotettix, as well as of fruit pests of the family of the Diaspididae with the genus Aonidiella, of the family of the Tortricidae with the genus Adoxophyes, and of the family of the Olethreutidae with the genera Cydia and Lobesia.

The preparation of substituted alkyl esters of 2-(4-phenoxyphenoxy)ethylcarbamic acid and the use thereof for controlling phytophagous insects is disclosed in European patent application 0 004 334 and in UK patent application 2 084 574 A. In the fomer publication, ethyl 2-[4-(4-chlorophenoxy)phenoxy]ethylcarbamate is named as preferred individual compound.

Surprisingly, compared with this prior art, it has been found that ethyl 2-[4-(3-chlorophenoxy)phenoxy]ethylcarbamate is excellently suited to controlling cicadas which feed on rice crops, for example Niliparvata lugens, Nephotettix cincticeps and Nephotettix virescens, as well as to controlling various fruit pests, especially Tortricidae such as Adoxophyes reticulana (fruit tortix moth), Cydia pomonella (codling moth) or Lobesia botrana (grape-berry moth), scales in citrus fruit crops such as Aonidiella aurantii (California red scale), and whiteflies in cotton and vegetables, such as Bemisia tabaci and Trialeurodes vaporariorum. The ethyl 2-[4-(3-chlorophenoxy)phenoxy]ethylcarbamate used in the practice of this invention is principally effective as chemosterilant or population inhibitor and as ovicide.

In addition to the above mentioned particularly advantageous effects, ethyl 2-[4-(3-chlorophenoxy)phenoxy]ethylcarbamate is also effective against the following pests:

of the order Lepidoptera, for example:

Amylois spp., Coleophora spp., Yponomeuta spp., Prays spp., Lyonetia spp., *Keiferia lycopersicella, Pectinophora gossypiella, Plutella xylostella, Leucoptera scitella*, Lithocollethis spp., Aegeria spp., Synanthedon spp., Adoxophyes spp., Pieris spp., Archips spp., Argyrotaenia spp., Choristoneura spp., Pandemis spp., Sparganothis spp., Cnephasia spp., Acleris spp., Tortrix spp., Cochylis spp., *Eupoecilia ambiguella, Hedya nubiferana, Lobesia botrana*, Eucosma spp., Cydia spp., Grapholita spp., Pammene spp., Malacosoma spp., Manduca sexta, Chilo spp., Diatraea spp., Crocidolomia binotalis, Ostrinia nubilalis, *Cadra cautella*, Ephestia spp., Operophtera spp., Thaumetopoea spp., Euproctis spp., Lymantria spp., Agrotis spp., Euxoa spp., *Mamestra brassicae, Panolis flammea, Busseola fusca*, Sesamia spp., Spodoptera spp., Heliothis spp., Earias spp., Autographa spp., *Trichoplusia ni, Cryptophlebia leucotreta, Phthorimaea operculella, Diparopsis castanea, Alabama argillaceae, Anticarsia gemmatalis* and *Hellula undalis*, Cnaphalocrocis spp., Scirpophaga spp., Hyphantria cunea, *Carposina nipponensis, Phtorimaea operculella, Cryptophlebia leucotreta, Clysia ambiguella* and *Pieris rapae*;

of the order Coleoptera, for example:

Sitotroga spp., *Leptinotarsa decemlineata*, Diabrotica spp., Agriotes spp., Anthonomus spp., Cosmopolites spp., Dermestes spp., Epilachna spp., Orycaephilus spp., Sitophilus spp., Otierhynchus spp., Tribolium spp., Tenebrio spp., Melolontha spp., Popillia spp., Rhizopertha spp., Trogoderma spp., Curculio spp., Eremnus spp. und Phlyctinus spp., Lissorhoptrus spp., *Chaetocnema tibialis*, Psylliodes spp., *Atomaria linearis* and Scarabeidae;

of the order Orthoptera, for example:

Blatta spp., Periplaneta spp., Leucophaea maderae, Blattella spp., Gryllotalpa spp., Locusta spp. and Schistocerca spp.;

of the order Isoptera, for example:

Reticulitermes spp.;

of the order Psocoptera, for example:

Liposcelis spp.;

of the order Anoplura, for example:

Phylloxera spp., Pemphigus spp., Pediculus spp., Haematopinus spp. and Linognathus spp.;

of the order Mallophaga, for example:

Trichodectes spp. und Damalinea spp.;

of the order Thysanoptera, for example:

Hercinothrips spp., Thrips tabaci, Taeniothrips spp. und Scirtothrips aurantii, Frank Liniella spp. and Thrips palmi;

of the order Heteroptera, for example:

Eurygaster spp., Dysdercus spp., Piesma spp., Cimex spp., Rhodnius spp., Triatoma spp., Nezzara spp., Scotinophara spp., Leptocorisa spp., Euchistus spp., *Sahlbergella singularis* and *Distantiella theobroma;* of the order Homoptera, for example:

*Aleurodes brassicae, Bemisia tabaci, Trialeurodes vaporariorum*, Aphididae, Empoasca spp., Nephotettix spp., Laodelphax spp., Nilaparvata spp., Aonidiella spp., *Lecanium corni*, Saissetia spp., Aspidiotus spp., Pseudococcus spp., Planococcus spp., Pseudaulacaspis spp., Quadraspidiotus spp., Psylla spp., *Chrysomphalus aonidium, Aleurothrixus floccosus, Trioza erytreae, Eriosoma larigerum, Unaspis citri*, Ceroplaster spp. und Partatoria spp., Lepidosaphes spp., Erythroneura spp., Gascardia spp., *Coccus hesperidum, Pulvinaria aethiopica*, Schizaphis spp., Aphis spp., Sitobion spp., Macrosiphus spp., Rhopalosiphum spp., Myzus spp., Pemphigus spp., Scaphoideus spp. and *Chrysophalus dictyospermi;* of the order Hymenoptera, for example:

Diprion spp., Hoplocampa spp., Lasius spp., *Monomorium pharaonis*, Vespa spp., Neodiprion spp. and Solenopsis spp., Atta spp., Acromyrex, Diprionidae, *Gilpinia polytoma* und Cephus spp.;

of the order Diptera, for example:

Aedes spp., Culex-spp., *Drosophila melanogaster*, Musca spp., Fannia spp., *Calliphora erythrocephala*, Lucilia spp., Chrysomyia spp., Cuterebra spp., Glossina spp., Gastrophilus spp., Hyppobosca spp., Stomoxys spp., Oestrus spp., Hypoderma spp., Tabanus spp., Tannia app., *Bibio hortulanus, Oscinella frit*, Phorbia spp., *Pegomyia hyoscyami*, Ceratitis spp., Dacus spp., Tipula spp., Liriomyza spp., Melanagromyza spp., *Antherigona soccata*, Sciara spp., *Rhagoletis pomonella* and Orseolina spp.;

of the order Siphonaptera, for example:

*Xenopsylla cheopis* and Ceratophyllus spp.;

of the order of the Acarina, for example:

Panonychus spp., Tetranychus spp., Tarsonemus spp., *Bryobia praetiosa, Acarus siro*, Argas spp., Ornithodoros spp., *Dermanyssus gallinae*, Eriophyes spp., *Phyl-*

*locoptruta oleivora*, Boophilus spp., Rhipicephalus spp., Amblyomma spp., Hyalomma spp., *Ixodes* spp., Psoroptes spp., Chorioptes spp., Saracoptes spp., Aceria sheldoni, *Polyphagotarsonemus latus, Eotetranychus carpini* und Brevipalpus spp., Calipitrimerus spp., *Aculus schlechtendali*, Rhizoglyphus spp. und *Olygonychus pratensis* and of the order of the Thysanura, for example:
Lepisma saccharina.

Further, the ethyl 2-[4-(3-chlorophenoxy)phenoxy]ethylcarbamate can also be used for controlling phytophagous nematodes and snails.

The carbamate used in the practice of this invention can be prepared by the process disclosed in European patent application 0 004 334.

Thus the ethyl 2-[4-(3-chlorophenoxy)phenoxy]ethylcarbamate of formula I

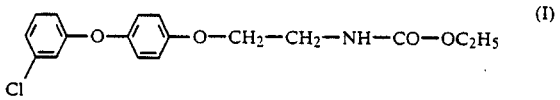

can be obtained, for example, by a) reacting the 4-(3-chlorophenoxy)phenol of formula II

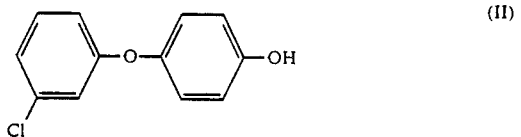

in the presence of a base and in an inert organic solvent, with an ethyl 2-ethylcarbamate of formula III

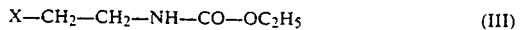

wherein X is a leaving group such as a halogen atom or a sulfonyloxy group, preferably chloro, bromo, methylsulfonyloxy or p-tolylsulfonyloxy, or b) reacting the 2-[4-(3-chlorophenoxy)phenoxy]ethylamine of formula IV

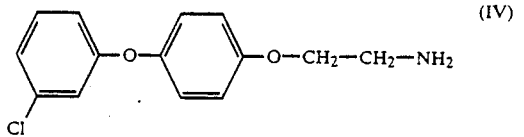

in the presence of a base, with the ethyl chloroformate of formula V

Suitable bases for the reaction (II+III→I) are preferably inorganic bases such as alkali metal carbonates, alkali metal alkoxides, alkali metal hydroxides or alkali metal hydrides, alkali metal bicarbonates such as sodium carbonate, potassium carbonate, sodium hydrogencarbonate, potassium hydrogencarbonate or tertiary amines. Preferred solvents are aprotic polar solvents such as dialkyl amides such as dimethyl formamide, also dioxane, tetrahydrofuran, dimethoxyethane, dimethyl sulfoxide or sulfolane, or mixtures thereof. The reaction temperature is normally in the range from −20° C. and the boiling point of the reaction mixture. The reaction temperature will preferably be above +60° C., most preferably in the boiling range of the chosen solvent. It has been found useful to add a catalytic amount of an alkali metal iodide such as potassium iodide. In highly polar solvents such as dimethyl sulfoxide or sulfolane it is possible to carry out the reaction in the presence of a base as indicated above in the temperature range from +10° C. to +50° C., preferably from +20° C. to +40° C.

In the reaction (IV+V→I) suitable bases are preferably tertiary amines such as trialkylamines, for example triethylamine or N-ethyldiisopropylamine, pyridine, dialkylaminopyridine such as dimethylaminopyridine or dialkylanilines such as N,N-dimethylaniline. The reaction is normally carried out in the temperature range from −20° C. to +100° C. A particularly suitable temperature range is that from −20° C. to +100° C. The reaction is conveniently carried out in an organic solvent. Representative examples of more suitable solvents are: ethers such as diethyl ether, dimethoxyethane, tetrahydrofuran or dioxane, hydrocarbons such as toluene, benzene, xylenes, hexane or the different petroleum fractions, or chlorinated hydrocarbons such as methylene chloride, chloroform, dichloroethane or trichloroethane.

The starting compounds of formulae II, III, IV and V are known and some are commercially available.

The insecticidal activity of the ethyl 2-[4-(3-chlorophenoxy)phenoxy]ethylcarbamate can be substantially broadened and adapted to prevailing circumstances by addition of other insecticides and/or acaricides. Examples of suitable additives include: organophosphorus compounds, nitrophenols and derivatives thereof, formamidines, ureas, pyrethroids, carbamates, and chlorinated hydrocarbons.

The good pesticidal activity of the ethyl 2-[4-(3-chlorophenoxy)phenoxy]ethylcarbamate corresponds to a mortality of at least 50-60% of the noxious insects to be controlled.

The ethyl 2-[4-(3-chlorophenoxy)phenoxy]ethylcarbamate used in the practice of this invention is used in unmodified form, or preferably together with the adjuvants conventionally employed in the art of formulation, and are therefore formulated in known manner to emulsifiable concentrates, directly sprayable or dilutable solutions, dilute emulsions, wettable powders, soluble powders, dusts, granulates, and also encapsulations in e.g. polymer substances. As with the compositions, the methods of application such as spraying, atomising, dusting, scattering or pouring, are chosen in accordance with the intended objectives and the prevailing circumstances.

The formulations, i.e. the compositions, preparations or mixtures containing the insecticide and, where appropriate, a solid or liquid adjuvant, are prepared in known manner, e.g. by homogeneously mixing and/or grinding the active ingredient with extenders, e.g. solvents, solid carriers and, in some cases, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol, ethylene glycol monomethyl or monoethyl ether, ketones such as cyclohexanone, strongly polar solvents such as N-methyl-2-pyrrolidone, dimethyl sulfoxide or dimethyl formamide, as well as vegetable oils or epoxidised vegetable oils such as epoxidised coconut oil or soybean oil; or water.

The solid carriers used e.g. for dusts and dispersible powders are normally natural mineral fillers such as calcite, talcum, kaolin, montmorillonite or attapulgite. To improve the physical properties it is also possible to add highly dispersed silicic acid or highly dispersed absorbent polymers. Suitable granulated adsorptive carriers are porous types, for example pumice, broken brick, sepiolite or bentonite; and suitable nonsorbent carriers are materials such as calcite or sand. In addition, a great number of pregranulated materials of inorganic or organic nature can be used, e.g. especially dolomite or pulverised plant residues.

Depending on the type of formulation, suitable surface-active compounds are non-ionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained, e.g. from coconut oil or tallow oil. Further suitable surfactants are also the fatty acid methyltaurin salts.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammonium salts and generally contain a $C_8$–$C_{22}$-alkyl radical which also includes the alkyl moiety of acyl radicals, e.g. the sodium or calcium salt of lignosulfonic acid, of dodecylsulfate, or of a mixture of fatty alcohol sulfates obtained from natural fatty acids. These compounds also comprise the salts of sulfated and sulfonated fatty alcohol/ethylene oxide adducts. The sulfonated benzimidazole derivatives preferably contain 2 sulfonic acid groups and one fatty acid radical containing about 8 to 22 carbon atoms. Examples of alkylarylsulfonates are the sodium, calcium or triethanolamine salts of dodecylbenzenesulfonic acid, dibutylnaphthalenesulfonic acid, or of a condensate of naphthalenesulfonic acid and formaldehyde. Also suitable are corresponding phosphates, e.g. salts of the phosphated adduct of p-nonylphenol with 4 to 14 moles of ethylene oxide.

Non-ionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols. Further suitable non-ionic surfactants are the water-soluble adducts of polyethylene oxide with polypropylene glycol, ethylenediaminopolypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil thioxilate, polypropylene/polyethylene oxide adducts, tributylphenoxypolyethoxyethanol, polyethylene glycol and octylphenoxypolyethoxyethanol. Fatty acid esters of polyoxyethylene sorbitan, e.g. polyoxyethylene sorbitan trioleate, are also suitable non-ionic surfactants.

Cationic surfactants are preferably quaternary ammonium salts which contain, as N-substituent, at least one $C_8$–$C_{22}$alkyl radical and, as further substituents, unsubstituted or halogenated lower alkyl, benzyl or hydroxy-lower alkyl radicals. The salts are preferably in the form of halides, methylsulfates or ethylsulfates, e.g. stearyltrimethylammonium chloride or benzyl bis(2-chloroethyl)ethylammonium bromide.

The surfactants customarily employed in the art of formulation are described e.g. in the following publications:

"1985 International Mc Cutcheon's Emulsifiers & Detergents", Glen Rock NJ USA, 1985", H. Stache, "Tensid-Taschenbuch" (Handbook of Surfactants), 2nd. ed., C. Hanser Verlag Munich/Vienna 1981, M. and J. Ash. "Encyclopedia of Surfactants", Vol. I–III, Chemical Publishing Co., New York, 1980–1981.

The pesticidal compositions usually contain 0.1 to 99%, preferably 0.1 to 95%, of ethyl 2-[4-(3-chlorophenoxy)phenoxy]ethyl carbamate, 1 to 99.9% of a solid or liquid adjuvant, and 0 to 25%, preferably 0.1 to 20%, of a surfactant.

Whereas commercial products are preferably formulated as concentrates, the end user will normally employ diluted formulations of substantially lower concentration. Typical rates of concentration are from 0.01 to 1000 ppm, preferably from 0.01 to 500 ppm. The rates of application per hectare are in general from 0.1 to 1000 g per hectare, preferably from 1 to 500 g/ha.

Preferred formulations are composed in particular of the following constituents (%=percentage by weight):

| Emulsifiable concentrates | |
|---|---|
| insecticide: | 1 to 50%, preferably 5 to 30% |
| surfactant: | 5 to 30%, preferably 10 to 20% |
| liquid carrier: | 20 to 94%, preferably 50 to 85% |
| Dusts | |
| insecticide: | 0.1 to 10%, preferably 0.1 to 1% |
| solid carier: | 99.9 to 90%, preferably 99.9 to 99% |
| Suspension concentrates | |
| insecticide: | 5 to 75%, preferably 10 to 50% |
| water: | 94 to 25%, preferably 90 to 30% |
| surfactant: | 1 to 40%, preferably 2 to 30% |
| Wettable powders | |
| insecticide: | 0.5 to 90%, preferably 1 to 80% |
| surfactant: | 0.5 to 20%, preferably 1 to 15% |
| solid carrier: | 5 to 95%, preferably 15 to 90% |
| Granulates | |
| insecticide: | 0.5 to 30%, preferably 3 to 15% |
| solid carrier: | 99.5 to 70%, preferably 97 to 85%. |

The compositions can also contain further ingredients such as antifoams, preservatives, viscosity regulators, binders, tackifiers and fertilisers or other chemical agents to obtain special effects.

The invention is illustrated by the following non-limitative Examples.

EXAMPLE 1A

Preparation of ethyl 2-[4-(3-chlorophenoxy)phenoxy]ethylcarbamate

To a solution of 13.2 g of 4-(3-chlorophenoxy)phenol (m.p. 53°–54° C.) are added 16.6 g of finely powdered potassium carbonate, 13.6 g of ethyl 2-chloroethylcarbamate and 1 g of powdered potassium iodide. With stirring, the reaction mixture is heated to +95° C. over 15 hours and then filtered. The filtrate is taken up in ice-water and extracted three times with ether. The organic extracts are washed with water, dried over sodium sulfate and concentrated by evaporation. The crude product is purified by chromatography over silica gel with a 1:3 mixture of ether/hexane to give the pure ethyl 2-[4-(3-chlorophenoxy)phenoxy]ethylcarbamate of m.p. 45°–46° C. The $^1$H-NMR spectrum is in conformity with the indicated structure.

EXAMPLE 1B

With stirring, a solution of 13 g of ethyl chloroformate in 20 ml of toluene is added dropwise to a solution of 24.8 g of 2-[4-(3-chlorophenoxy)phenoxy]ethylamine and 16.8 g ethyl diisopropylamine in 150 ml of toluene, and the mixture is thereafter stirred for 15 hours at this temperature. After cooling to room temperature, the reaction mixture is washed in succession with water, 1N hydrochloric acid and, finally, with a solution of sodium chloride and dried over sodium sulfate. The solvent is removed by vacuum distillation and the crude product is further purified by chromatography over silica gel with a 1:3 mixture of diethyl ether/hexane, affording the pure ethyl 2-[4-(3-chlorophenoxy)phenoxy]ethylcarbamate of m.p. 45°–46° C. The product so obtained is identical with that obtained in Example 1A.

EXAMPLE 2

Action against *Nilaparvata lugens*

Rice plants are treated with an aqueous emulsion-spray formulation containing the test compound in a concentration of 400 to 0.2 ppm. After the spray coating has dried, the rice plants are populated with cicada larvae in the 2nd and 3rd stage. Evaluation is made 21 days later. The percentage reduction of the population (% age mortality) is determined by comparing the number of surviving cicadas on the treated plants with those on the untreated plants.

In this test, the activity of the ethyl 2-[4-(3-chlorophenoxy)phenoxy]ethylcarbamate is 80–100% at a concentration of 0.2 ppm, whereas the isomeric ethyl 2-[4-(4-chlorophenoxy)phenoxy]ethylcarbamate of EP 0 004 334 has the same activity only when used in a concentration of at least 400 ppm.

EXAMPLE 3

Ovicidal action against *Cydia pomonella*

Eggs of *Cydia pomonella* laid on filter paper are immersed for a brief time in an aqueous acetonic solution containing the test compound in a concentration of 400 to 0.01 ppm. After the test solution has dried, the eggs are incubated in petri dishes. The percentage hatching rate of the eggs compared with untreated controls is determined 6 days later (percentage reduction of hatching).

In this test, the activity of the ethyl 2-[4-(3-chlorophenoxy)phenoxy]ethylcarbamate against *Cydia pomonella* is 80–100% at a concentration of 0.01 ppm.

EXAMPLE 4

Ovicidal action against *Adoxophyes reticulana*

Eggs of *Adoxophyes reticulana* laid on filter paper are immersed for a brief time in an aqueous acetonic solution containing the test compound in a concentration of 400 to 0.05 ppm. After the test solution has dried, the eggs are incubated in petri dishes. The percentage hatching rate of the eggs compared with untreated controls is determined 6 days later (percentage reduction of hatching).

In this test, the activity of the ethyl 2-[4-(3-chlorophenoxy)phenoxy]ethylcarbamate against *Adoxophyes reticulana* is still 80–100% even at a concentration of 0.05 ppm, whereas the isomeric ethyl 2-[4-(4-chlorophenoxy)phenoxy]ethylcarbamate has this activity only at a concentration of at least about 50 ppm.

EXAMPLE 5

Ovicidal action against *Lobesia botrana*

Eggs of *Lobesia botrana* deposited on filter paper are immersed for a brief time in an aqueous acetonic solution containing the test compound in a concentration of 400 ppm. After the test solution has dried, the eggs are incubated in petri dishes. The percentage hatching rate of the eggs compared with untreated controls is determined 6 days later (percentage reduction of hatching).

In this test, the ethyl 2-[4-(3-chlorophenoxy)phenoxy]ethylcarbamate exhibits good activity against Lobesia botrana.

EXAMPLE 6

Action against *Aonidiella aurantii*

Potato tubers are populated with *Aonidiella aurantii* crawlers (California red scale). After ca. 2 weeks, the potatoes are immersed in a spray mixture prepared from an aqueous emulsion or suspension containing the test compound in a concentration of 400 ppm. After the treated potato tubers have dried, they are incubated in plastic containers. Evaluation is made 10–12 weeks later by comparing the survival rate of the crawlers of the first filial generation of the treated population with that of the untreated controls.

In this test, the ethyl 2-[4-(3-chlorophenoxy)phenoxy]ethylcarbamate exhibits good activity against *Aonidiella aurantii*.

EXAMPLE 7

Action against *Boophilus microplus*

Replete adult females are fixed with adhesive tape to a PVC sheet and covered with a cotton wool swab. The test organisms are then treated by impregnating the cotton wool swab with 10 ml of an aqueous solution containing the test compound in a concentration of 125 ppm. The cotton wool swab is then removed and the ticks are incubated for 4 weeks for oviposition. The action against Boophilus microplus is observed either as kill or sterility of the females or takes the form of ovicidal action against the eggs.

In this test, the ethyl 2-[4-(3-chlorophenoxy)phenoxy]ethylcarbamate exhbits good activity against *Boophilus microplus*.

EXAMPLE 8

Action against *Aedes aegypti*

50-100 Aedes aegypti larvae are put into 200 ml of an aqueous test solution which contains 400 ppm of the test compound and a very small amount of feed. The container is then sealed with a top and incubated. Evaluation is made 14 days later for percentage hatching of the adults in comparison with untreated control batches.

In this test, the ethyl 2-[4-(3-chlorophenoxy)phenoxy]ethylcarbamate exhibits good activity against *Aedes aegypti*.

EXAMPLE 9

Action against *Nephotettix cincticeps*

Rice plants are treated with an aqueous emulsion spray formulation containing the test compound in a concentration of 400 ppm. After the spray coating has dried, the rice plants are populated with cicada larvae in the 2nd and 3rd stage. Evaluation is made 21 days later. The percentage reduction of the population (% age mortality) is determined by comparing the number of surviving cicadas on the treated plants with those on the untreated plants.

In this test, the ethyl 2-[4-(3-chlorophenoxy)phenoxy]ethylcarbamate exhibits good activity against Nephotettix cincticeps.

EXAMPLE 10

Action against *Bemisia tabaci*

Dwarf beans are placed in gauze cages and populated with adults of *Bemisia tabaci* (white flies). After oviposition, all the adults are removed and 10 days later the plants with the nymphs present thereon are treated with an emulsion spray mixture containing the test compound in a concentration of 400 ppm. Evaluation of the hatching rate is made 14 days after application in comparison with untreated controls.

In this test, the ethyl 2-[4-(3-chlorophenoxy)phenoxy]ethylcarbamate exhibits good activity against *Bemisia tabaci*.

EXAMPLE 11

Insecticidal formulations of ethyl 2-[4-(3-chlorophenoxy)phenoxy]ethylcarbamate
(throughout, percentages are by weight)

| F1. Wettable powders | a) | b) | c) |
| --- | --- | --- | --- |
| compound of formula I | 25% | 50% | 75% |
| sodium ligninsulfonate | 5% | 5% | — |
| sodium laurylsulfate | 3% | — | 5% |
| sodium diisobutylnaphthalenesulfonate | — | 6% | 10% |
| octylphenol polyethylene glycol ether (7-8 mol of ethylene oxide) | — | 2% | — |
| highly dispersed silicic acid | 5% | 10% | 10% |
| kaolin | 67% | 27% | — |

The insecticide is thoroughly mixed with the adjuvants and the mixture is thoroughly ground in a suitable mill, affording wettable powders which can be diluted with water to give suspensions of the desired concentration.

| 2. Emulsifiable concentrate | a) | b) |
| --- | --- | --- |
| compound of formula I | 10% | 10% |
| octylphenol polyethylene glycol ether (4-5 mol of ethylene oxide) | 3% | — |
| calcium dodecylbenzenesulfonate | 3% | — |
| castor oil polygycol ether (36 mol of ethylene oxide) | 4% | — |
| castor oil thioxilate | — | 25% |
| cyclohexanone | 30% | — |
| butanol | — | 15% |
| xylene mixture | 50% | — |
| ethyl acetate | — | 50% |

Emulsions of any required concentration can be obtained from this concentrate by dilution with water.

| 3. Dusts | a) | b) |
| --- | --- | --- |
| compound of formula I | 5% | 8% |
| talcum | 95% | — |
| kaolin | — | 92% |

Ready for use dusts are obtained by mixing the insecticide with the carrier, and grinding the mixture in a suitable mill.

| 4. Extruder granulate | |
| --- | --- |
| compound of formula I | 10% |
| sodium ligninsulfonate | 2% |
| carboxymethylcellulose | 1% |
| kaolin | 87% |

The insecticide is mixed and ground with the adjuvants, and the mixture is subsequently moistened with water. The mixture is extruded and then dried in a stream of air.

| 5. Coated granulate | |
| --- | --- |
| compound of formula I | 3% |
| polyethylene glycol (mol. wt. 200) | 3% |
| kaolin | 94% |

The finely ground is uniformly applied, in a mixer, to the kaolin moistened with polyethylene glycol. Non-dusty coated granulates are obtained in this manner.

| 6. Suspension concentrate | |
| --- | --- |
| compound of formula I | 40% |
| ethylene glycol | 10% |
| nonylphenol polyethylene glycol ether (15 mol of ethylene oxide) | 6% |
| sodium ligninsulfonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground insecticide is intimately mixed with the adjuvants, giving a suspension concentrate from which suspen-sions of any desired concentration can be obtained by dilution with water.

What is claimed is:

1. A method of controlling *phytophagous cicadas* in rice crops, which comprises contacting or treating said pests or their development stages or the locus thereof with a pesticidally effective amount of ethyl 2-[4-(3-chlorophenoxy)phenoxy]ethylcarbamate or with a composition which contains a pesticidally effective amount of said compound.

2. A method according to claim 1 for controlling *phytophagous cicadas* of the families Delphacidae and Cicadillidae.

3. A method of controlling phytophagous leaf rollers in fruit crops, which comprises contacting or treating said pests or their development stages or locus thereof with a pesticidally effective amount of the ethyl 2-[4-(3-chlorophenoxy)phenoxy]ethylcarbamate or with a composition which contains a pesticidally effective amount of said compound.

4. A method according to claim 3 for controlling fruit, citrus fruit and vine pests of the families Diaspididae, Tortricidae or Olethreutidae.

5. A method of controlling scale insects in fruit crops, which comprises contacting or treating said pests or their development stages or the locus thereof with a pesticidally effective amount of the ethyl 2-[4-(3-chlorophenoxy)phenoxy]ethylcarbamate or with a composition which contains a pesticidally effective amount of said compound.

6. A method of controlling noctuids and white flies in cotton and vegetable crops, which comprises contacting or treating said pests or their development stages or the locus thereof with a pesticidally effective amount of the ethyl 2-[4-(3-chlorophenoxy)phenoxy]ethylcarbamate or with a composition which contains a pesticidally effective amount of said compound.

7. A method according to claim 6 for controlling pests of the families Noctuidae and Aleyrodidae in cotton and vegetable crops.

8. A method according to claim 1 for controlling *phytophagous cicadas* of the genera Nilaparvata and Nephotettix in rice crops.

9. A method according to claim 1 for controlling *Nilaparvata lugens* in rice crops.

10. A method according to claim 3 for controlling fruit, citrus fruit and vine pests of the genera Aonidiella, Adoxophyes, Cydia or Lobesia.

11. A method according to claim 3 for controlling fruit, citrus fruit and vine pests selected from Cydia pomonella, Adoxophyes reticulana or Lobesia botrana.

12. A method according to claim 6 for controlling pests of the genera Heliothis, Spodoptera, Bemisia and Trialeurodes in cotton and vegetable crops.

13. A method according to claim 6 for controlling pests selected from the genera *Heliothis virescens, Heliothis zea, Heliothis armigera, Spodoptera littoralis, Spodoptera exigua, Bemisia tabaci* or *Trialeurodes vaporariorum* in cotton and vegetable crops.

14. A method according to claim 5 for controlling *Aonidiella auranti* in fruit crops.

* * * * *